United States Patent
Salzer (10) Patent No.: US 11,808,733 B2
(45) Date of Patent: Nov. 7, 2023

(54) SQUARE WAVE AMPEROMETRY ALKALINITY MEASUREMENT

(71) Applicant: Hach Company, Loveland, CO (US)

(72) Inventor: Corey Alan Salzer, Fort Collins, CO (US)

(73) Assignee: HACH COMPANY, Loveland, CO (US)

(*) Notice: Subject to any disclaimer, the term of this patent is extended or adjusted under 35 U.S.C. 154(b) by 142 days.

(21) Appl. No.: 17/143,700

(22) Filed: Jan. 7, 2021

(65) Prior Publication Data

US 2022/0214306 A1 Jul. 7, 2022

(51) Int. Cl.
*G01N 27/416* (2006.01)

(52) U.S. Cl.
CPC ................. *G01N 27/4167* (2013.01)

(58) Field of Classification Search
CPC .. G01N 27/308; G01N 27/4167; G01N 27/44; G01N 27/49; G01N 31/16; G01N 31/164
See application file for complete search history.

(56) References Cited

U.S. PATENT DOCUMENTS

| 2007/0111202 A1 | 5/2007 | Henkens et al. |
| 2018/0224397 A1* | 8/2018 | Kroll .................... G01N 27/302 |
| 2020/0400610 A1 | 12/2020 | Rajasekharan et al. |
| 2021/0341418 A1 | 11/2021 | Salzer et al. |

OTHER PUBLICATIONS

B.G. Cox, Square-Wave Amperometry, J. Electroanal. Chem., 1982(136), p. 93-104. (Year: 1982).*
Brian G. Cox et al., "Square-Wave Amperometry", J. Electroanal. Chem., Jun. 10, 1982, 12 pages, vol. 136, No. 1, Elsevier Sequoia S.A., The Netherlands.

* cited by examiner

*Primary Examiner* — Caitlyn Mingyun Sun
(74) *Attorney, Agent, or Firm* — Ference & Associates LLC (57) ABSTRACT

An embodiment provides a method for measuring an alkalinity of an aqueous sample, including: introducing an aqueous sample to a voltammetric pH electrode; holding the potential of a voltammetric pH electrode at a pH end point potential; applying a voltage step waveform comprising at least one potential pulse to the voltammetric pH electrode; titrating the aqueous sample; and measuring a current output resulting from the voltage step waveform, wherein the measuring comprises square wave amperometry. Other aspects are described and claimed.

9 Claims, 7 Drawing Sheets

SQUARE WAVE AMPEROMETRY ALKALINITY MEASUREMENT

FIELD

This application relates generally to water quality measurement, and, more particularly, to measurement of alkalinity in an aqueous sample.

BACKGROUND

Ensuring water quality is critical in a number of industries such as pharmaceuticals and other manufacturing fields. Additionally, ensuring water quality is critical to the health and well-being of humans, animals, and plants which are reliant on the water for survival. One parameter of the water that may be measured is the alkalinity. Measurement of alkalinity may allow for identification or computation of other parameters of the water, for example, buffering capacity of the water, which allows for identifying the overall quality of the water. One method to test for alkalinity includes a complex titration process, requires chemicals to be added to the sample, and also a longer time to measure alkalinity.

BRIEF SUMMARY

In summary, one embodiment provides a method for measuring an alkalinity of an aqueous sample, comprising: introducing an aqueous sample to a voltammetric pH electrode; holding the potential of a voltammetric pH electrode at a pH end point potential; applying a voltage step waveform comprising at least one potential pulse to the voltammetric pH electrode; titrating the aqueous sample; and measuring a current output resulting from the voltage step waveform, wherein the measuring comprises square wave amperometry.

Another embodiment provides a device for measuring an alkalinity of an aqueous sample, comprising: a voltammetric pH electrode; at least one reference electrode; at least one auxiliary electrode; and a memory storing instructions executable by a processor to: introduce an aqueous sample to the voltammetric pH electrode; hold the potential of a voltammetric pH electrode at a pH end point potential; apply a voltage step waveform comprising at least one potential pulse to the voltammetric pH electrode; titrate the aqueous sample; and measure a current output resulting from the voltage step waveform, wherein the measuring comprises square wave amperometry.

A further embodiment provides a system for measuring an alkalinity of an aqueous sample, comprising: a voltammetric pH electrode; at least one reference electrode; at least one auxiliary electrode; and a storage device having code stored therewith, the code being executable by the processor and comprising: code that introduces an aqueous sample to a voltammetric pH electrode; code that holds the potential of a voltammetric pH electrode at a pH end point potential; code that applies a voltage step waveform comprising at least one potential pulse to the voltammetric pH electrode; code that titrates the aqueous sample; and code that measures a current output resulting from the voltage step waveform, wherein the measuring comprises square wave amperometry.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The measurement of the alkalinity of water or other aqueous solution or sample is very common and allows for determination of the quality of the aqueous solution. Typical water quality analysis tests for alkalinity are often performed manually using time consuming titrations. A conventional alkalinity measurement technique requires that a user manually add a strong acid to the aqueous sample to determine, by titration, the alkalinity of the sample. One technique requires a careful addition of sulfuric acid into a solution and the determination of an endpoint that can be correlated to the alkalinity of the sample. While some alkalinity measurement instruments are available, these instruments are expensive, complex, and not responsive enough for online monitoring or control.

Another online alkalinity measurement system performs alkalinity measurements using an electrochemical cell. Such an online alkalinity determination system may use electrochemical reactions for producing the acid (i.e., protons) in situ. These online electrochemical methods may generate protons in situ through oxidation of water within the sample itself. In this system, the proton generation can be correlated to the alkalinity of the water. For example, the proton generation is generally calculated based on the electron flow assuming for each electron passed, one H+ is generated. The generation of protons in situ from the sample eliminates the need for metering reagents such as acid delivery in a manual titration reaction. Thus, online electrochemical titration methods may be easier to use and do not require concentrated acid.

Conventional methods of voltammetric measurement of pH have used electrodes with chemical moieties, such as quinones, anthraquinones, etc on an electrode surface or in solution. The potential of the working electrode may be changed over time and the maximum or minimum potential of the current output is correlated with the sample pH. One approach is the utilization of square wave voltammetry for measurement of pH using voltammetric pH electrodes. For example, square wave voltammetry (SWV) is a form of linear potential sweep voltammetry that may use combined square wave and ramped potential applied to a stationary electrode. There may be advantages to utilizing this pulsed-scanning method, such as reduction in non-faradaic currents, sensitivity, rapid sweep times and in the case of voltammetric pH sensors, easily defined peaks. What is needed is a more rapid and direct determination of an end point in a coulometric titration using a voltammetric pH electrode.

Accordingly, the systems and methods described herein provide a technique for alkalinity measurement. In an embodiment, an aqueous sample alkalinity may be measured using a voltammetric pH electrode. The voltammetric pH electrode may be a boron-doped diamond (BDD) material. In an embodiment, the voltammetric pH electrode may be held at a potential bias voltage corresponding to a titration end point potential. A voltage step waveform may be applied using at least one potential pulse to the voltammetric pH electrode. In an embodiment, the voltage step waveform may have a forward and a backward component. The voltage step waveform may comprise peak amplitudes that are consistent over time. The aqueous sample may be titrated. The titration may comprise the addition of protons which may be generated in-situ or added as an acid. In an embodiment, a current output may be measurement. In an embodiment, a portion of the current output from a portion of the voltage step may be measured. In an embodiment, the current output may reach a maximum at the titration end point potential. The measuring may be continuous or intermittent. Full scan square wave voltammetry (SWV) for obtaining the peak potential from the current response and correlating that to a pH value may take ~10 seconds or longer to perform. In an embodiment, at least one potential step or several potential step cycles run faster than having to run full SWV scans.

The illustrated example embodiments will be best understood by reference to the figures. The following description is intended only by way of example, and simply illustrates certain example embodiments.

Figure 1:
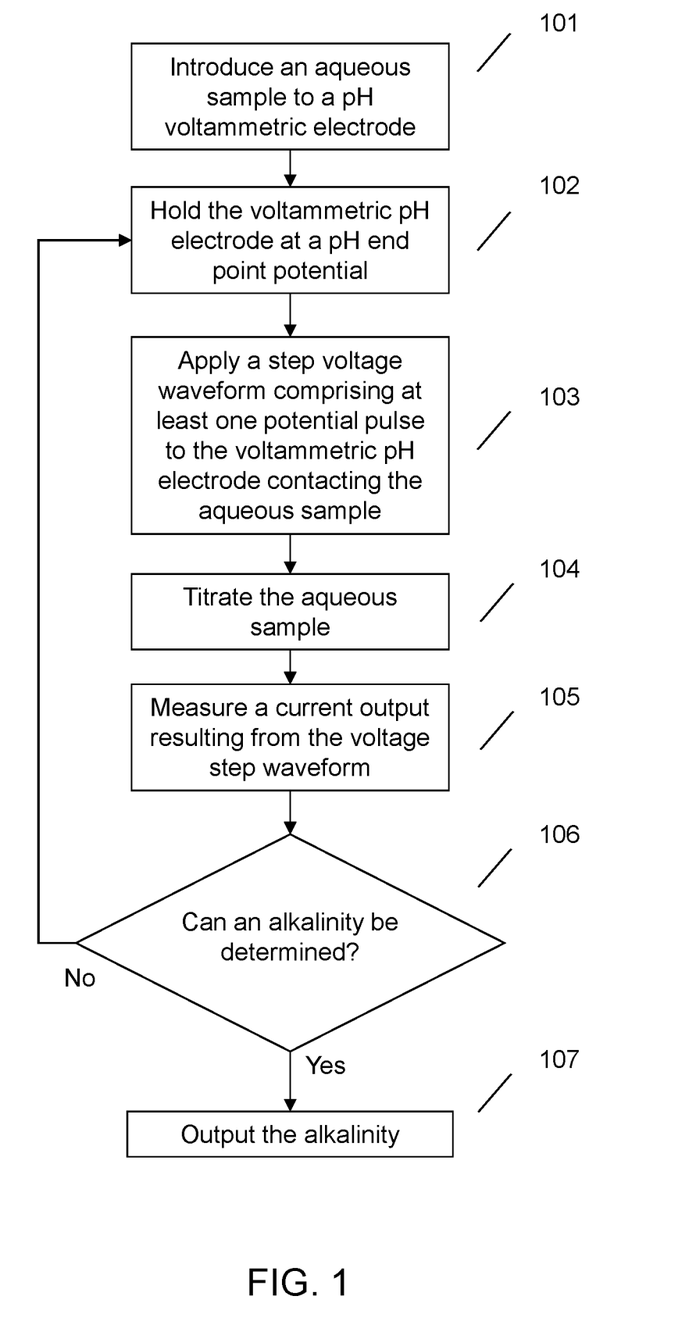
FIG. 1 illustrates a flow diagram of measuring alkalinity in an aqueous sample.

Referring to FIG. 1, an embodiment may measure an alkalinity of an aqueous sample. Traditional approaches may use full scan SWV for obtaining the peak potential from the current response and correlating that to a pH value. These scans may take ~10 seconds or longer to perform. The scans may occur between acid generation or addition steps. In an embodiment, full scans may not be required to be performed and may run faster than having to run full SWV scans.

At 101, in an embodiment, an aqueous sample may be introduced into a test chamber. The aqueous sample may be placed or introduced into a test chamber manually by a user or using a mechanical means, for example, gravity flow, a pump, pressure, fluid flow, or the like. For example, a water sample for alkalinity testing may be introduced to a chamber by a pump. In an embodiment, there may be one or more chambers in which the one or more method steps may be performed. In an embodiment, valves or the like may control the influx and efflux of the aqueous solution into or out of the one or more chambers, if present. Once the sample is introduced to the measurement system, the system may measure the pH of the sample. This pH value may be used to determine whether the sample has a pH at or below the titration end point. For example, the pH value may indicate that the titration end point values may be between pH 4.5 and pH 4.3 or lower, indicating no alkalinity in the sample.

In an embodiment, the electrodes may be fully or at least partially disposed in the volume of aqueous solution. For example, if the aqueous solution is introduced into a chamber having one or more electrodes, the aqueous solution may at least partially cover the one or more electrodes. As another example, the one or more electrodes may be partially disposed within the chamber with the other portion of the electrode outside the chamber. Thus, when the aqueous solution is introduced into the chamber it only covers the portion of the electrodes that are within the chamber.

Figure 2:
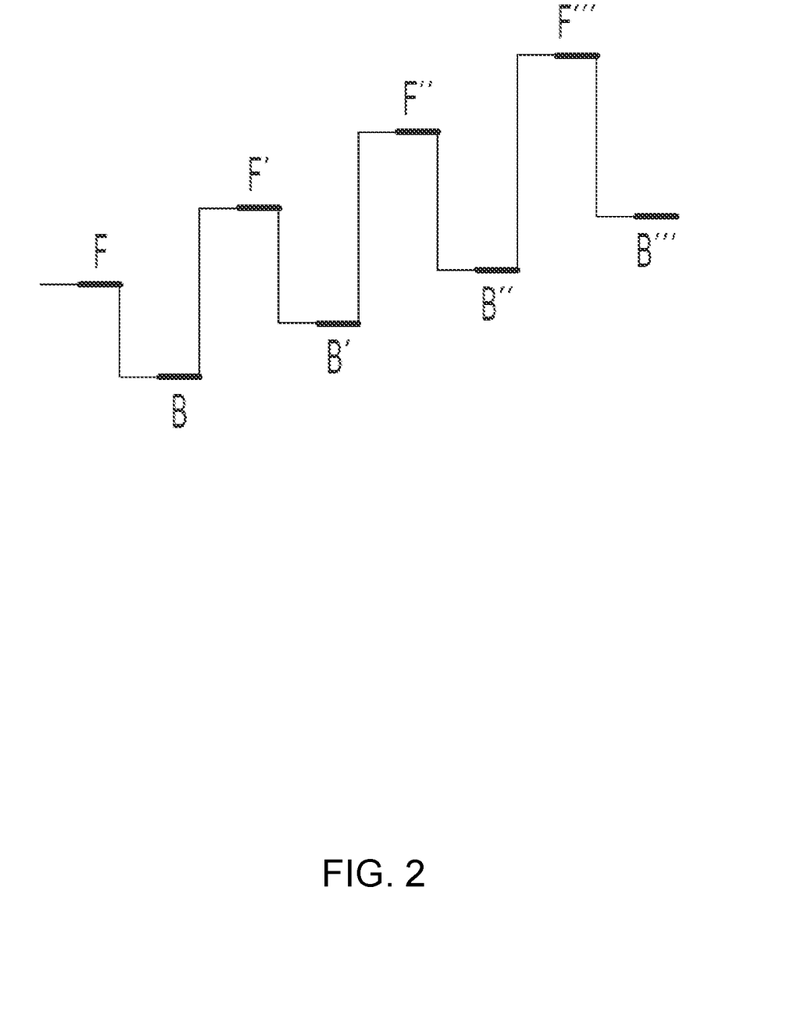
FIG. 2 illustrates an example step-wise protocol for measuring alkalinity in an aqueous sample.
Figure 3:
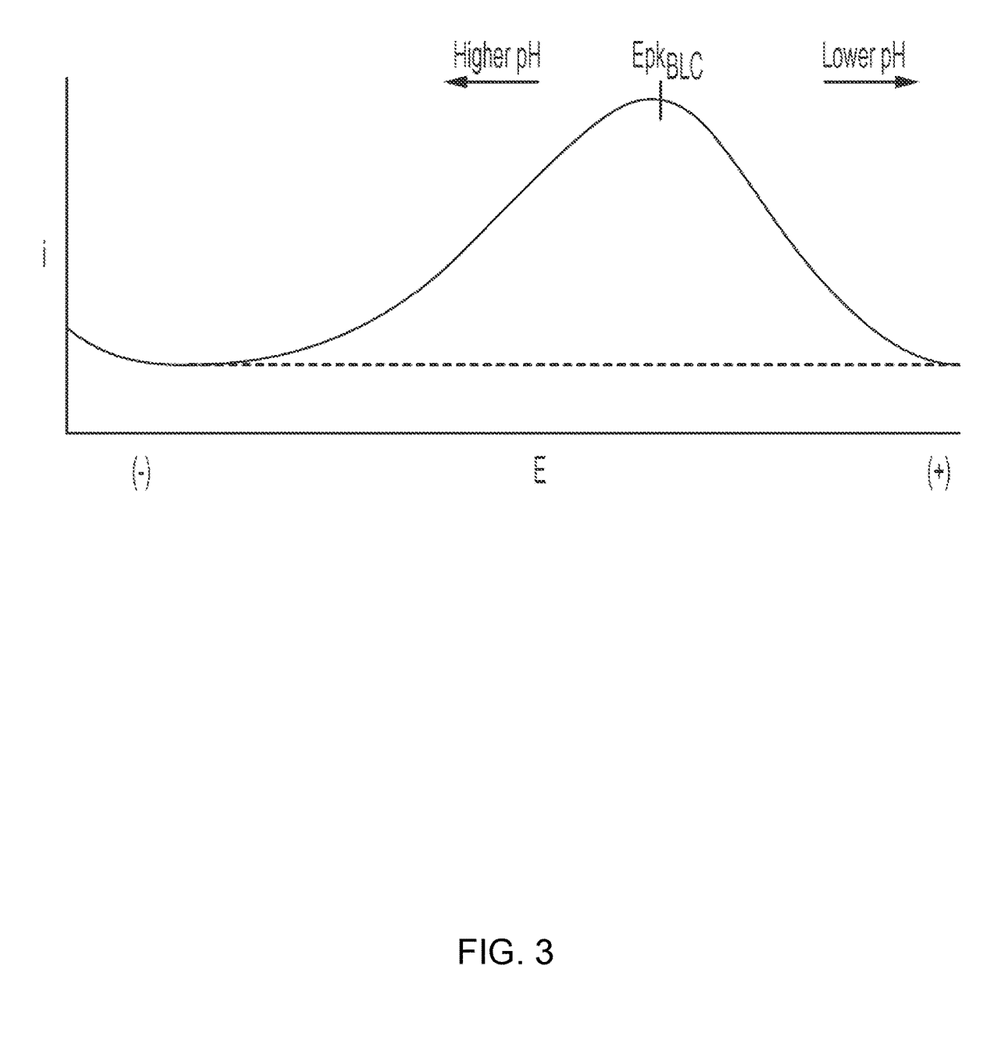
FIG. 3 illustrates an example of a square wave voltammetry current-voltage plot in an aqueous sample.

At 102, in an embodiment, the method and system may hold the voltammetric pH electrode at a pH end point bias potential. Instead of performing square wave voltammetry (SWV) which may include a series of pulsed steps on a ramped sweep potential (FIG. 2) to produce a SWV plot (FIG. 3), the system and method may perform square wave amperometry (SWA) as described herein. For example, the voltammetric pH electrode may hold or clamp the bias voltage at an end point potential prior to performing a titration. The end point potential corresponding to a potential value related to a pH end point value.

At 103, in an embodiment, the system may apply a voltage step waveform. In an embodiment, the voltage step waveform may comprise one or more eaves, pulses, potential pulses, or the like. In an embodiment, the voltage may be referred to as an electrical signal. The electrical signal may be applied using one or more electrodes, for example, a series of electrodes. Electrodes may include a working electrode, counter (auxiliary) electrode, reference electrode, or the like. In an embodiment, the electrode may comprise a pH sensitive voltammetric electrode. In an embodiment, the one or more series of electrodes may be boron doped diamond (BDD) electrodes. Other electrode material are disclosed and contemplated. The use of BDD may serve as a better electrode material than other carbon-based or metallic materials (e.g., silver, gold, mercury, nickel, etc.) because these materials may eventually themselves become oxidized, thereby generating interfering signals and contributing to the errors in the measurement of alkalinity. Thin film BDD electrodes may undergo thermal stress because of the different thermal expansion coefficients between the substrate and the BDD layer, which limits the current density that can be applied to these electrodes. Thick BDD solid electrodes do not have the substrate and therefore the structural and electrical integrity may be maintained at a higher current. The lack of substrate in the thick, solid, free-standing BDD electrode eliminates the problem of delamination that can occur on thin-filmed BDD materials.

Figure 4:
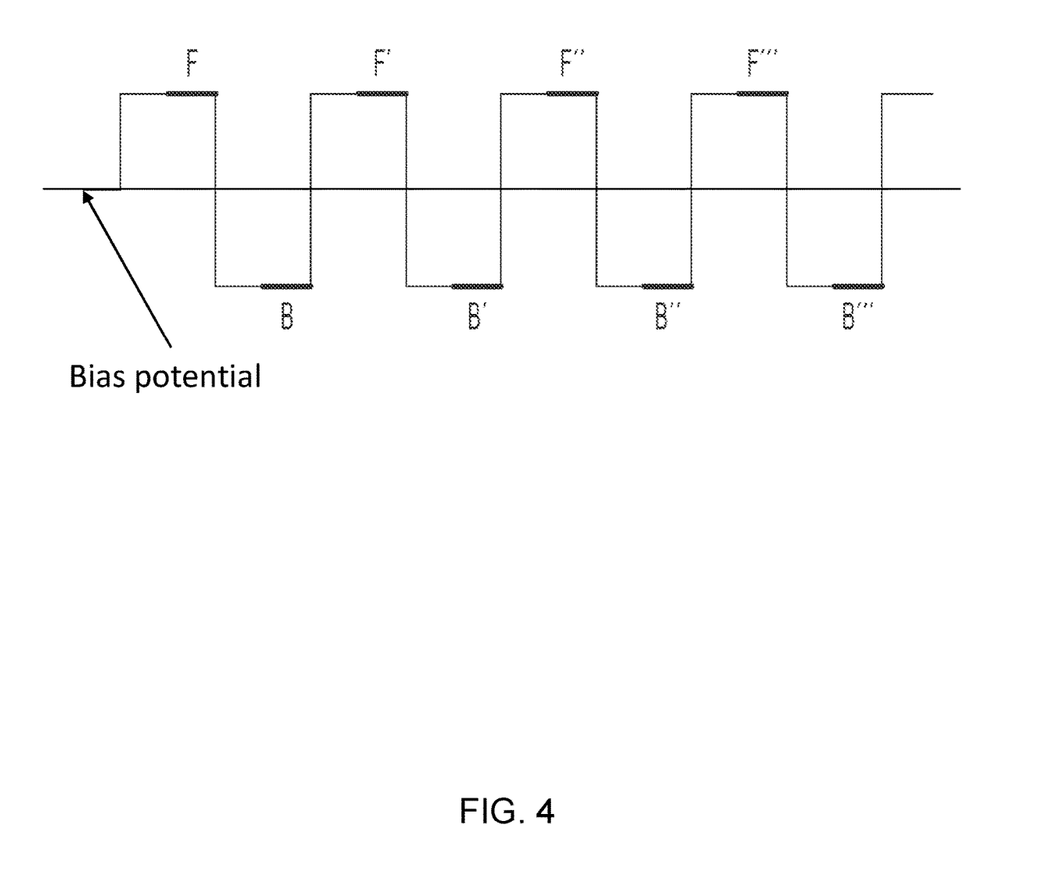
FIG. 4 illustrates an example of a square wave amperometry step-wise voltage protocol for measuring alkalinity in an aqueous sample.

In an embodiment, the voltage step waveform may be a series of voltage steps of the same or similar amplitude. In an embodiment, a symmetric square wave potential perturbation may be applied to the potential bias at the voltammetric pH electrode producing current responses which correlate to the pH redox response of the electrode. A series of titration steps are performed at intervals with corresponding intervals of voltage step perturbations and current output values until a current response maximum is observed. In this manner, each subsequent forward (F) and backward (B) pulse has an amplitude equal to or nearly equal to the preceding corresponding forward and backward amplitude. Each subsequent pulse is denoted with an additional prime superscript (FIG. 4). In an embodiment, an advantage of the method is a faster alkalinity measurement. In part, this may result from measuring only one or only a few step potential cycles instead of a full square wave voltammogram over a wide potential range.

The applied electrical signal may be any electrical signal selected from a waveform group, for example, a pulse, a step, a sawtooth, a sine wave, a square, a triangle, or the like or any combination thereof. Thus, the applied electrical signal may be applied as continuous pulses or intermittent electrical signals. Response optimization may be accomplished for a sample by selective choice of electrical signal amplitude and/or period. The electrical signal may be a preprogrammed waveform, may be altered during a measurement, and/or may be controlled by the system or by a user.

At 104, in an embodiment the method and system may titrate the aqueous sample. In an embodiment, protons may be added to the aqueous sample. For example, protons may be added using an acid, such as in a liquid form. Alternatively, proton may be generated in-situ. One or more electrodes may be designed to function at a potential to generate protons. The system may wait at the applied signal and/or apply subsequent electrical signal after the measurement of current output at 103 to generate an amount of protons to neutralize buffer capacity that facilitates the determination of alkalinity.

Figure 5:
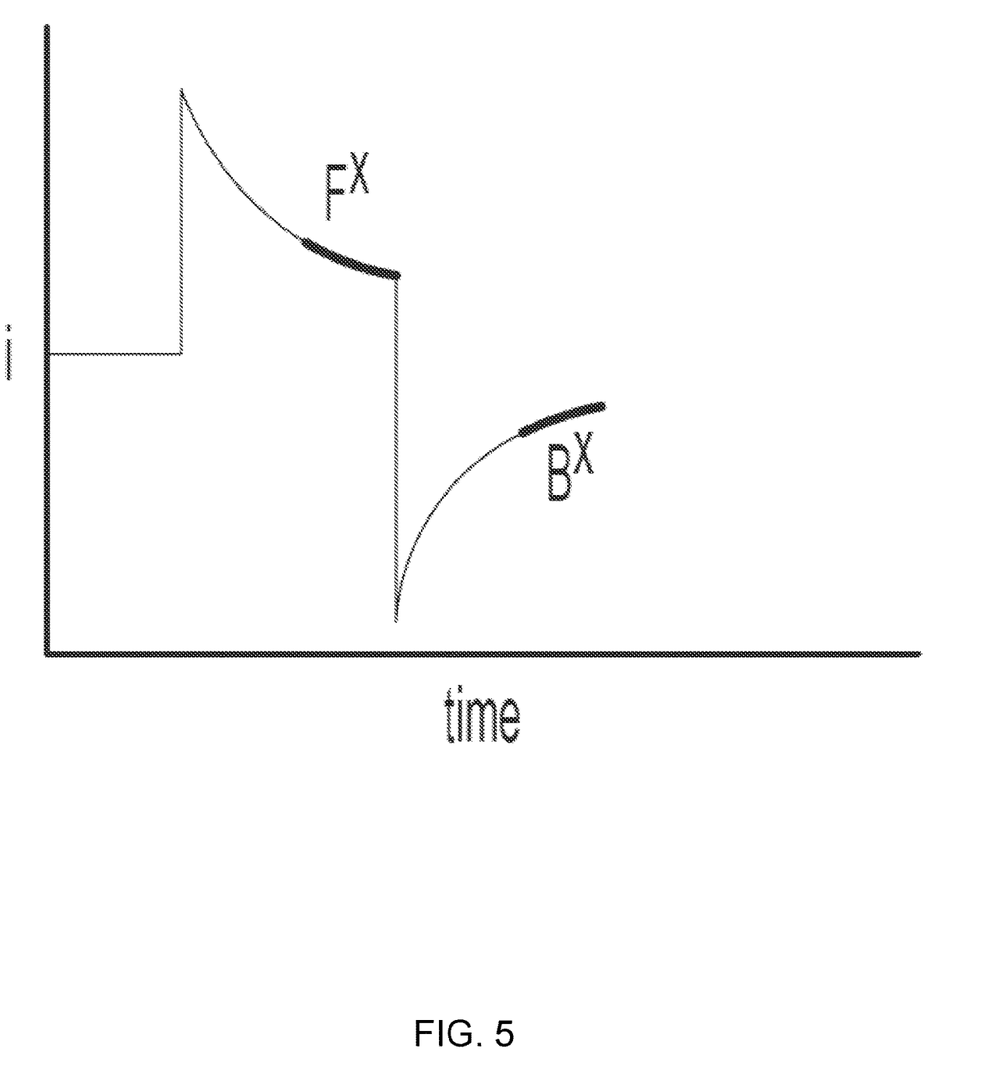
FIG. 5 illustrates an example current plot for measuring alkalinity in an aqueous sample.
Figure 6A:
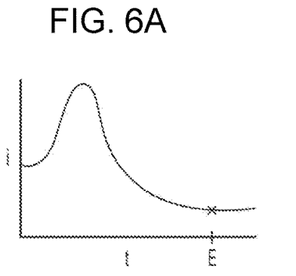
FIG. 6A illustrates a sample current at a given time for an end point.
Figure 6B:
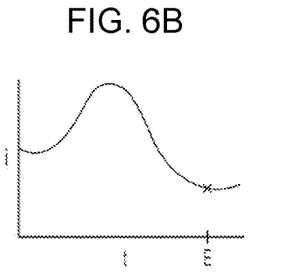
FIG. 6B illustrates a sample current at a given time for an end point.
Figure 6C:
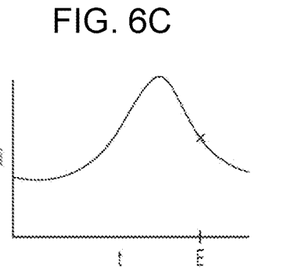
FIG. 6C illustrates a sample current at a given time for an end point.
Figure 6D:
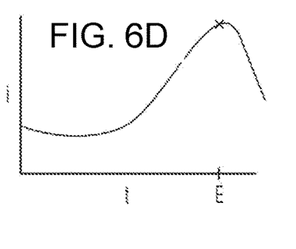
FIG. 6D illustrates a sample current at a given time for an end point.
Figure 6E:
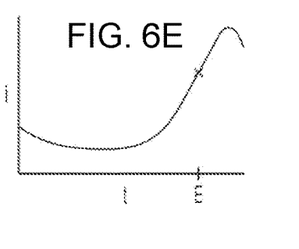
FIG. 6E illustrates a sample current at a given time for an end point.
Figure 6F:
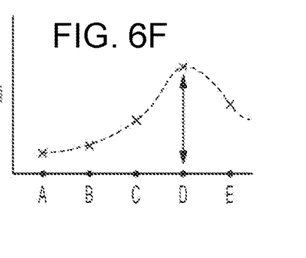
FIG. 6F illustrates a summary of data from FIG. 6A through FIG. 6E.

At 105, in an embodiment, the method and system may measure a current output. In an embodiment, the measuring may be based upon a portion of the voltage step waveform and/or a portion of the current output. Referring to FIG. 5, an example current output is illustrated. For example, a forward (F) and a backward (B) current is shown corresponding to a forward and backward voltage perturbation around the bias voltage of the voltammetric pH electrode. In an embodiment, a portion of the current output is used to determine the current. As an example, the portion used is depicted as a darkened or thickened portion of the current trace. Other durations or intervals may be used for measurement, and the illustrated trace is an example. In this manner, the method and system may measure a current and perform an alkalinity measurement in a faster time. Additionally, a system measuring, sorting, and calculating the data may have less computational burden which may allow for faster results and calculation.

Referring to FIG. 6, in an embodiment, a series of square wave voltammetry current-potential plots are illustrated at intervals over the span of a titration. For example, as the titration progresses from FIG. 6A through FIG. 6E, the square wave voltammogram peak shifts to the right. The rightward shift denotes a decrease in sample pH. A simple example of a square wave voltammetry response is provided in FIG. 3. In this square wave amperometry method described herein, the measured current response is indicated by an 'x' on the plots in FIG. 6A-6E at the bias end point potential. Collection of the 'x' indicated current values at the corresponding titration intervals produces the plot in FIG. 6F. As an example, the current plots may be made into a composite trace such as that shown in FIG. 6F which demonstrates the peak of the current at point D corresponding to FIG. 6D with a maximum current at the end point.

In an embodiment, the pH electrode may be held at the titration end point potential with a square voltage step waveform applied around that end point potential having a certain magnitude and frequency. The current output may be determined in a similar fashion to SWV. For example, a differential current between the forward and backward step may be determined using a portion of the current output for each potential pulse. For a period of no change in the sample pH, the current output would be a stable value. If acid were added or generated in the sample, and the square voltage step waveform on a bias potential was applied to the voltammetric pH electrode, the current output would be generally stable until the pH of the sample approached the titration end point potential. For example, as the pH approaches the end point the current output will increase until it reaches a maximum at the pH corresponding to the end point and then decrease again as the pH further decreases. The SWA can be operated continuously or intermittently and correlate with the acid addition/generation steps. In the intermittent mode, a few cycles would be sufficient to obtain the current output and be much faster than performing a whole SWV sweep.

The method and system, at 106, may determine an alkalinity. This determination may be made based upon the amount of protons added/generated and a current value measurement response in the aqueous sample. In other words, after obtaining a current response maximum, the system may measure the acid added to reach the current maximum and the system may correlate this value to an alkalinity. If a maxima has not been obtained in the plotted titration response at 106, the system may continue to apply an electrical signal and measure the response of the system at 105 until the alkalinity is determined.

If, however, the alkalinity may be determined at 106, the system, at 107, may output an alkalinity of the aqueous sample. The alkalinity measurement may be based upon a comparison of the current observed and acid added to the sample. In an embodiment, an alkalinity of a sample may be based upon a number of protons generated in an aqueous sample. Alkalinity may be quantified as M-alkalinity (a.k.a Total Alkalinity), P-Alkalinity, or the like. M-alkalinity may be a measure of the amount of acid or protons requires to drop a sample pH to a value of about 4.3. P-alkalinity may be a measure of the amount of acid or protons required to drop a sample pH to a value of about 8.3. In an embodiment, instead of using harsh acid reagents that may need to be added or titrated by a user, an embodiment generates proton through an electrochemical process, for example, by applying an electrical signal to the aqueous solution. Accordingly, the systems and methods as described herein provide a technique for the electrochemical generation of protons that serve as a source for protons instead of the addition or titration of an acid (e.g., sulphuric acid) as required in traditional techniques.

In an embodiment, an output may be in the form of a display, storing the data to a memory device, sending the output through a connected or wireless system, printing the output, or the like. The system may be automated, meaning the system may automatically output the electrode. The system may also have associated alarms, limits, or predetermined thresholds. For example, if a measured peak-to-peak separation reaches a threshold, the system may trigger an alarm, alert the system/personnel to a fault, alter the flow of the aqueous solution, or the like. Data may be analyzed in real-time, stored for later use, or any combination thereof.

The various embodiments described herein thus represent a technical improvement to conventional methods and instrument for alkalinity measurement. Using the techniques as described herein, an embodiment may use a method and device for an instrument for alkalinity measurement in a faster time frame. This is in contrast to conventional methods with limitations mentioned above. Such techniques provide a better method to construct and an instrument for alkalinity measurement.

Figure 7:
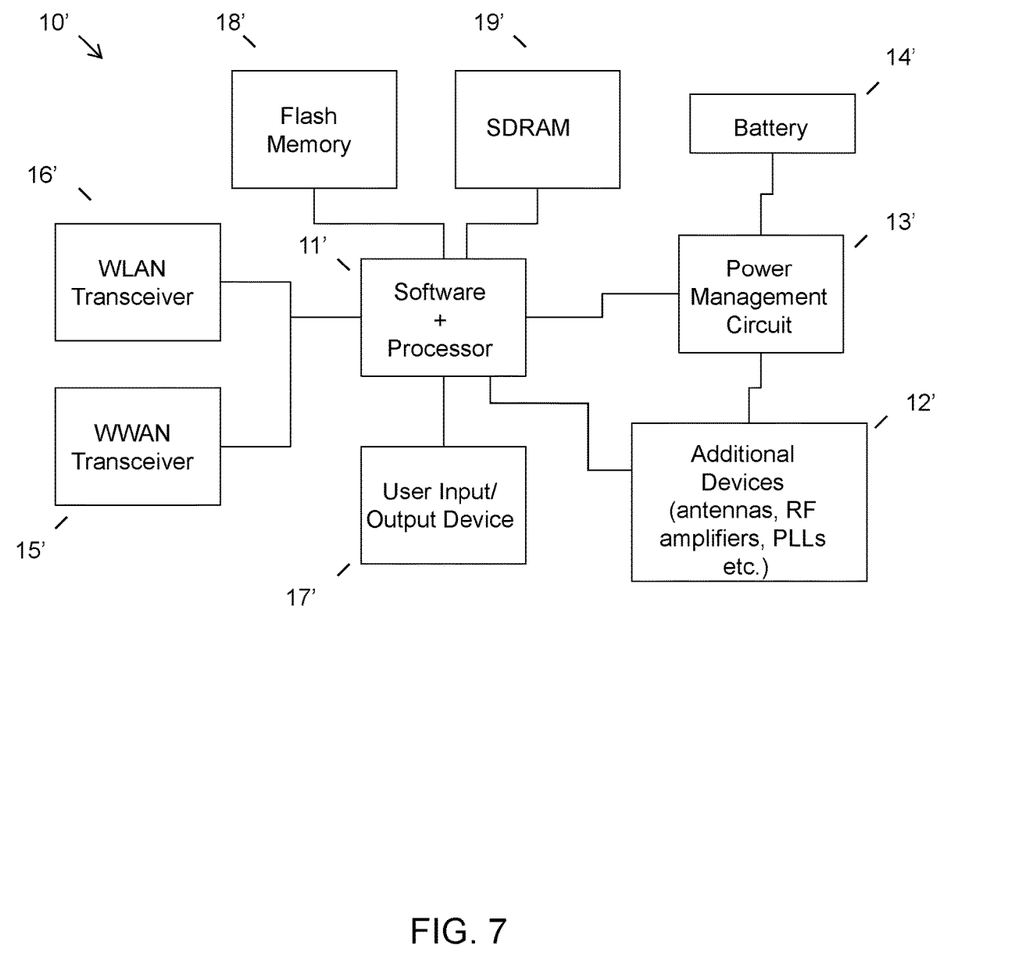
FIG. 7 illustrates an example of computer circuitry.

While various other circuits, circuitry or components may be utilized in information handling devices, with regard to an instrument for alkalinity measurement according to any one of the various embodiments described herein, an example is illustrated in FIG. 7. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment of an instrument for alkalinity measurement.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring an alkalinity of an aqueous sample, comprising:
   introducing the aqueous sample to a voltammetric pH electrode;
   holding a potential of the voltammetric pH electrode at a pH end point bias potential, wherein the pH end point bias potential corresponds to a titration pH end point;
   applying a voltage step waveform comprising a plurality of potential pulses to the voltammetric pH electrode;
   titrating the aqueous sample;
   measuring one or a few current outputs resulting from the plurality of potential pulses, wherein the measuring comprises square wave amperometry; and
   plotting a series current outputs from the voltage step waveform over a time span of the titrating to obtain a current maximum value.

2. The method of claim 1, wherein the voltammetric pH electrode comprises a boron doped diamond material.

3. The method of claim 1, wherein the voltage step waveform comprises pulsed potential steps.

4. The method of claim 1, wherein the titrating comprises an addition of protons to the aqueous sample, wherein the addition of protons is selected from the group consisting of: in-situ generation and acid addition.

5. The method of claim 4, wherein the addition of protons correlates to the alkalinity of the aqueous sample.

6. The method of claim 1, wherein the measuring comprises a differential output current for each potential pulse between at least a portion of a forward step and at least a portion of a backward step.

7. The method of claim 1, wherein the measuring further comprises a mode selected from the group consisting of: continuous measurement and intermittent measurement.

8. The method of claim 7, wherein the mode correlates to the titrating.

9. The method of claim 1, wherein the voltage step waveform comprises square wave potential perturbations applied to the voltammetric pH electrode to produce current responses which correlate to a pH redox response of the electrode.

* * * * *